United States Patent [19]

Flynn et al.

[11] Patent Number: 5,057,495
[45] Date of Patent: Oct. 15, 1991

[54] ATRIAL HYPOTENSIVE PEPTIDE

[75] Inventors: Thomas G. Flynn; Donald B. Jennings, both of Kingston, Canada

[73] Assignee: Queen's University at Kingston, Kingston, Canada

[21] Appl. No.: 349,487

[22] Filed: May 9, 1989

Related U.S. Application Data

[63] Continuation-in-part of Ser. No. 242,145, Sep. 9, 1988, abandoned, which is a continuation-in-part of Ser. No. 100,047, Sep. 23, 1987, abandoned.

[30] Foreign Application Priority Data

Jun. 24, 1988 [CA] Canada .................................. 570432

[51] Int. Cl.$^5$ ........................ C07K 7/10; A61K 37/02
[52] U.S. Cl. ......................................... 514/12; 514/13; 530/324; 530/325; 530/326
[58] Field of Search ........................ 530/324, 326, 325; 514/12, 13

[56] References Cited

U.S. PATENT DOCUMENTS 4,904,763  2/1990  Matsuo et al. ...................... 530/324

OTHER PUBLICATIONS

Flynn, T. et al., *Biochem. and Biophys. Res. Commun.*, 161(2): 830–837, Jun. 1989.
Flynn, T. et al., Biochem. and Biophys. Res. Commun., 163(2): 1189, Sep. 1989.
Suggs, S. et al., *Proc. Natl. Acad. Sci.*, 78(11): 6613–6617, Nov. 1981.
Vlasuk, G. et al., *Biochenm. Biophys. Res. Commun.*, 136(1): 396–403, Apr. 1986.
Oikawa, S. et al., Biochem. Biophys. Res. Commun., 132(3): 892–899, Nov. 1985.
Kojima, M. et al., *Biochem. Biophys. Res. Commun.*, 159(3): 1420–1426, Mar. 1989.
Sudoh, T. et al., *Nature*, 332: 78–81, Mar. 1988.
Aburaya, M. et al., *Biochem. Biophys. Res. Commun.*, 163(1): 226–232, Aug. 1989.
Kamayashi, Y. et al., *Biochem. Biophys. Res. Commun.*, 163(1): 233–240, Aug. 1989.

*Primary Examiner*—Howard E. Schain
*Assistant Examiner*—Susan M. Perkins
*Attorney, Agent, or Firm*—Richard J. Hicks

[57] ABSTRACT

An atrial natriuretic peptide having profound natriuretic, diuretic and hypotensive effects, characterized by a 45 amino acid residue sequence:

Ser—Gln—Asp—Ser—Ala—Phe—Arg—Ile—Gln—Glu—
Arg—Leu—Arg—Asn—Ser—Lys—Met—Ala—His—Ser—
Ser—Ser—Cys—Phe—Gly—Gln—Lys—Ile—Asp—Arg—Ile—
Gly—Ala—Val—Ser—Arg—Leu—Gly—Cys—Asp—Gly—
Leu—Arg—Gln/Leu—Phe, having a disulphide bond between the cysteine residues which may be extracted from mammalian heart atria is described. A synthetic peptide comprising the above sequence of 45 amino acids and a synthetic 29 amino acid residue peptide corresponding to residues 17–45 of the above sequence both containing a disulfide linkage between the cysteine residues have also been prepared and shown to have similar biological activity as the native peptides. A synthetic 23 amino acid residue peptide corresponding to residues 23–29, which is the disulphide bonded ring portion of the above sequences, has been shown to have biological activity.

7 Claims, 6 Drawing Sheets iso-rANP[1-45]

```
         1                    10                   20                   30                   40   45
         S Q D S A F R I Q E R L R N S K M A H S S S C F G Q K I D R I G A V S R L G C D G L R Q F
                                             S━━━━━━━━━━━━━━━━━━━━━━━━━━━S
```

FIG. 3a iso-rANP / rANP / BNP

```
              1                    10                   20                   30                40    45
iso-rANP      S Q D S A F R I Q E R L R N S K M A H S S S C F G Q K I D R I G A V S R L G C D G L R Q F
              83          90                  100                 110                120            126
rANP          S A L L K S K L R A L L A G P R S L R R S S C F G G R I D R I G A Q S G L G C N S F R Y
              62      70                  80                  90                 100                106
BNP           P R S I F Q V L R G I R S P K T M R D S G C F G R R L D R I G S L S G L G C N V L R R Y
```

FIG. 3b

ATRIAL HYPOTENSIVE PEPTIDE

CROSS REFERENCE TO RELATED APPLICATIONS

This application is a continuation-in-part of our prior U.S. application Ser. No. 242,145 filed Sept. 9, 1988, non abandoned, which in turn is a continuation-in-part of U.S. application Ser. No. 100,047 filed Sept. 23, 1987 and now abandoned.

FIELD OF INVENTION

This invention relates to novel atrial hypotensive peptides and diagnostic kits therefor.

BACKGROUND OF INVENTION AND DESCRIPTION OF PRIOR ART

Since the description by deBold et al, Life Sci 28 89-94 (1981) of a potent atrial natriuretic factor extracted from rat atria, considerable attention has been directed to a family of diuretic and natriuretic peptides which have been shown to be stored in and secreted from mammalian atria. Attention is directed to deBold U.S. Pat. No. 4,663,437 issued May 5, 1987, Thibault et al U.S. Pat. Nos. 4,607,023 issued Aug. 19, 1986 and 4,455,864 issued Jan. 29, 1985 and Dec. 10, 1985 respectively. These references all teach atrial peptides having up to 71 amino acid residues in a sequence which always includes: Ser-Leu-Arg-Arg-Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg-Tyr or minor variations thereof depending on the atrial source (rat, human, etc.) and the precise method of isolation thereof. DeBold also established the existence of a disulphide bond between the cysteine residues and consequently the looped structure of the peptide. Recent sequence determinations by Needleman at al have shown (Science 1985; 229:397-400) the 28 amino acid peptide to be the circulating form of the peptide in humans. The human 28 amino acid peptide differs from the rat sequence only at position 110 at which position methionine occurs in the human peptide and isoleucine occurs in the rat peptide. These peptides, variously named ANF, cardionatrin, auriculin or atriopeptin, depending upon the authority, have been shown to exhibit profound diuretic, natriuretic and hypotensive effects of relatively short duration when injected into non-diuretic mammalian subjects, including man. These peptides are, therefore, of considerable interest and utility for therapeutic applications despite the lack of oral bioavailability and short half life of currently known analogs.

Initially ANF was produced by carboxylic extraction of rat heart atria, but as the amino-acid sequences were developed, most ANF peptides may now be produced synthetically. In the carboxylic acid extraction rat atria, either freshly dissected or frozen were obtained from standard commercial sources (i.e. diet of the rat is unimportant), finely ground in liquid nitrogen and extracted with a mixture of acetic acid and HCl containing phenyl methyl sufonyl fluoride in a homogenizer. After centrifugation the supernatant was passed through Sep-Pak cartridges and the cartridges were washed with trifluoroacetic acid (TFA) and eluted with acetonitrile in TFA. the eluates were reduced in volume and again separated on a $C_{18}$ column. The column was eluted with acetonitrite at different gradients.

Radioimmunoassays for ANF have also been developed in conventional manner by injection of chemically synthesized peptide, coupled to thyroglobulin, into rabbits for production of specific antisera. The antisera has then been combined into specific RIAs.

In the present specification the symbols for amino acids are according to standard IUPAC-IUB recommendations and single-letter symbols and three-letter symbols are used interchangeably for convenience according to the following table:

| A | Ala | Alanine | B | Asx | Asparagine or aspartic acid |
|---|---|---|---|---|---|
| C | Cys | Cysteine | D | Asp | Aspartic acid |
| E | Glu | Glutamic acid | F | Phe | Phenylalanine |
| G | Gly | Glycine | H | His | Histidine |
| I | Ile | Isoleucine | K | Lys | Lysine |
| L | Leu | Leucine | M | Met | Methionine |
| N | Asn | Asparagine | P | Pro | Proline |
| Q | Gln | Glutamine | R | Arg | Arginine |
| S | Ser | Serine | T | Thr | Threonine |
| V | Val | Valine | W | Trp | Tryptophan |
| Y | Tyr | Tyrosine | Z | Glx | Glutamine or glutamic acid |

SUMMARY OF THE INVENTION

During the course of experiments into ANF, and in particular cardionatrin extracted in conventional manner as briefly described above from rat atria it was noted that certain protein fractions eluting at about 33% $CH_3CN$ exhibited somewhat different diuretic, natriuretic and hypotensive responses to those normally associated with ANF. These fractions were, therefore purified to homogeneity by successive gradient-chromatography using TFA, hepta-fluorobutyric acid (HFBA) and ammonium acetate, and have been shown to have an entirely different composition to ANF. We have isolated a peptide, a 45 amino acid residue sequence:

Ser—Gln—Asp—Ser—Ala—Phe—Arg—Ile—Gln—Glu—

Arg—Leu—Arg—Asn—Ser—Lys—Met—Ala—His—Ser—Ser—

Ser—Cys—Phe—Gly—Gln—Lys—Ile—Asp—Arg—Ile—Gly—

Ala—Val—Ser—Arg—Leu—Gly—Cys—Asp—Gly—Leu—

Arg—Gln/Leu—Phe.

This sequence has a disulfide double bond between cysteine residues. This sequence, hereinafter designated iso-$rANF_{(1-45)}$ has not been found in a search in the Protein Data Banks of the National Library of Medicine and is, therefore, believed to be a novel peptide. The diuresis and natriuresis effects noted for this peptide are not due to the co-incident presence of ANF (ANP) because sequence analysis of the purified peptide does not reveal any ANP or pro-ANP sequence. Additionally, a peptide corresponding to the exact sequence of native iso-$rANP_{(1-45)}$ and containing a disulfide bond between residues 23 and 29 has been chemically synthesized and shown to exhibit potent diuretic, natriuretic and hypotensive effects. It is another object to synthesize a peptide corresponding to residues 17-45 of iso-$rANP_{(1-45)}$ including the disulfide bond, which is both analogous and homologous to $ANP_{(99-126)}$ and to the recently discovered pig brain natriuretic peptide (BNP). This peptide, hereinafter designated iso-$rANP_{(17-45)}$, elicits diuretic, natriuretic, hypotensive and bradycardic responses qualitatively similar to both the native peptide iso-$rANP_{(1-45)}$ and rat ANP (hereinafter r-ANP), when injected into bioassay rats. Thus isorANP(17-45) has an amino acid residue sequence comprising:

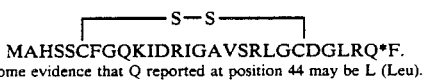
MAHSSCFGQKIDRIGAVSRLGCDGLRQ*F.
*There is some evidence that Q reported at position 44 may be L (Leu).

It is another object of this invention to provide a radioimmune assay and kit for detecting the 1-20 amino acid sequence of iso-rANP(1-45).

BRIEF STATEMENT OF INVENTION

By one aspect of this invention there is provided a peptide in substantially pure form selected from the group of peptides having the amino acid sequence $R_1$-Ser-Ser-Cys-Phe-Gly-Gln-Lys-Ile-Asp-Arg-Ile-Gly-Ala-Val-Ser-Arg-Leu-Gly-Cys-Asp-$R_2$-$R_3$ and a disulphide double bond between said Cys and wherein $R_1$ is H, Ser, His-Ser, Ala-His-Ser, Met-Ala-His-Ser or Ser-Gln-Asp-Ser-Ala-Phe-Arg-Ile-Gln-Glu-Arg-Leu-Arg-Asn-Ser-Lys-Met-Ala-His-Ser, $R_2$ is Gly, Gly-Leu, Gly-Leu-Arg, Gly-Leu-Arg-Gln/Leu, or Gly-Leu-Arg-Gln/Leu-Phe and $R_3$ is OH.

By a preferred aspect of this invention there is provided a peptide having an amino acid sequence:

Ser—Gln—Asp—Ser—Ala—Phe—Arg—Ile—Gln—Glu—
Arg—Leu—Arg—Asn—Ser—Lys—Met—Ala—His—Ser—
Ser—Ser—Cys—Phe—Gly—Gln—Lys—Ile—Asp—Arg—Ile—
Gly—Ala—Val—Ser—Arg—Leu—Gly—Cys—Asp—Gly—
Leu—Arg—Gln/Leu—Phe, with a disulfide bond between cysteine residues.

By another preferred aspect of this invention there is provided a peptide having an amino acid sequence:

Met—Ala—His—Ser—Ser—Ser—Cys—Phe—Gly—Gln—

Lys—Ile—Asp—Arg—Ile—Gly—Ala—Val—Ser—Arg—

Leu—Gly—Cys—Asp—Gly—Leu—Arg—Gln/Leu—Phe, with a disulphide bond between the Cys residues.

By another aspect of this invention there is provided a radioimmune assay and kit therefor, said kit comprising an antiserum to the 1-20 amino acid sequence of iso-rANP(1-45), an antigen consisting of a synthetic iso-rANP(1-20) having an added Tyr residue at the amino terminal serine (hereinafter iso-rANPY(1-20).

BRIEF DESCRIPTION OF DRAWINGS

FIG. 3a is a sketch illustrating the complete sequence of iso-rANP(1-45); and

FIG. 3b is a schematic comparison of the sequence of iso-rANP(1-45), with the C-terminal portions of pro-ANP and pro-BNP showing the large amount of homology which exists between all three in the vicinity of the disulfide ring.

DETAILED DESCRIPTION OF PREFERRED EMBODIMENTS

Figure 1A:
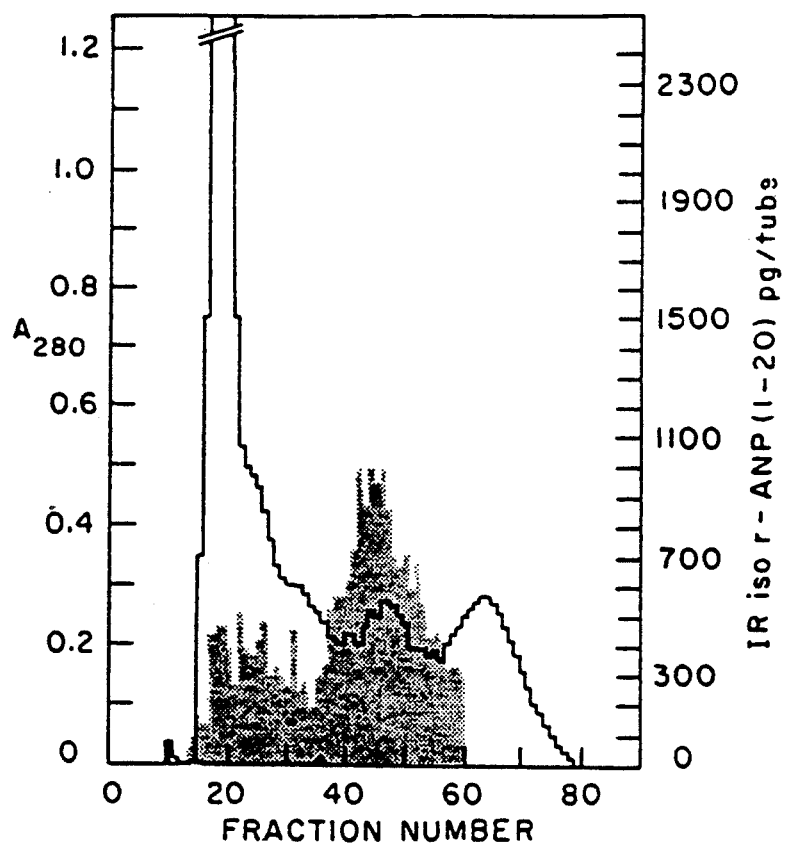
FIG. 1a is a biogel P10 chromatogram of lyophilized rat atrial extract for iso-rANP(1-45)

As noted above ANP(99-126) is the major circulating form of ANF and exerts its hormonal effects at receptor sites in kidney, smooth muscle, adrenal and other tissues. At least two types of ANP receptors have been identified. One ANP receptor is linked to particulate guanylate cyclase and mediates its action through cGMP while the other is not linked to guanylate cyclase and appears to be biologically silent. It has been suggested that the latter serves as a storage-clearance binding site for the hormone. Occupation of this so-called 'silent receptor' by a ring-depleted analogue of ANP causes an elevation in endogenous plasma ANP. This analogue is devoid of agonist and antagonist activity on the generation of cGMP but it competes effectively with biologically active atrial peptides for binding sites. Thus, an alternative to the storage-clearance role hypothesized for these receptors is that the 'silent' receptors are responsive to ANP-like peptides rather than to ANP itself.

The present peptides have resulted from this hypothesis. They are not directly related to ANP but have similar biological action. In the initial stages of the present development a peptide which co-eluted with a truncated form of pro-ANP on reverse phase HPLC of a rat atria extract was isolated and purified during the routine purification of pro-ANP and ANP, and when injected into assay rats, gave rise to a diuresis and natriuresis. This effect was not due to the co-incident presence of ANP because sequence analysis of the purfied peptide did not reveal any ANP or pro-ANP sequence. When sequenced by an automated gas phase sequencer the following amino acid sequence for the first 20 cycles of the sequencer was obtained: Ser-Gln-Asp-Ser-Ala-Phe-Arg-Ile-Gln-Glu-Arg-Leu-Arg-Asn-Ser-Lys-Met -Ala-His-Ser. A search of the Protein Data Bank of the National Biomedical Research Foundation revealed that this was a previously unknown sequence. The small amounts of this peptide that were available precluded extensive sequence analysis but amino acid composition of the peptide suggested a longer peptide. This, together with the biological activity and chemical uniqueness of the sequenced portion, indicated that the sequence was the amino terminal end of a new diuretic/natriuretic peptide.

Chemical synthesis of the 20 amino acid fragment was effected and anti-sera was raised in rabbits for the purpose of developing a specific radioimmunoassay (RIA).

The synthesis was conducted using standard solid-phase synthesis on a model 430 Applied Biosystems Peptide Synthesizer. The peptide was cleaved from the resin with hydrogen fluoride. Peptides were purified by semipreparative high performance liquid chromatography (HPLC) using a Vydac C$_{18}$ column. The composition and sequence of each peptide was verified by amino acid analysis on a Beckman 6300 automatic Amino Acid Analyzer and by gas-phase sequence analysis (Applied Biosystems Model 470A sequencer with on-line phenylthiohydantoin (PTH) analysis).

The procedure was repeated to produce the same 20 amino acid residue fragment with a tyrosine residue attached to the N-terminal serine. The 20-residue peptide (P2A) was mixed with Freund's complete adjuvant and injected subcutaneously into New Zealand white rabbits. After boosting at 5 weeks after the initial injection the rabbits were bled 1 week later. The anti-serum gave precipitin lines with its homologous antigen and with the native peptide extracted from atria when examined by double immunodiffusion. No cross reactivity under these conditions occurred with $ANP_{(99-126)}$, $ANP_{(101-126)}$ or with pro-ANP. Tyrosinated P2A (P2A-Y) was iodinated using the chloramine T method and the iodinated tracer was purified by HPLC on a Waters Bondapak $C_{18}$ column. For radioimmunossay (RIA) the buffer contained 0.1M $NaHPO_4$ buffer, pH 7.4, 0.05M NaCl, 0.1% BSA and 0.02% $NaCl_2$. The RIA incubation mixture contained 3-100 mg of P2A in 100 l of buffer, 100 μl of diluted antiserum and 100 l of $^{125}I$-P2A-Y (approx. 8000 cpm). After incubation overnight at 4° C. bound and free iodinated peptide were separated by second antibody precipitation using goat anti-rabbit $-\gamma$ globulin. The sensitivity of the assay was 2-3 pg/tube with 50% displacement at 25-30 pg/tube.

This antiserum did not cross-react with ANP or with pro-ANP. The RIA was then used to monitor the purification of the peptide de novo from atrial extracts using gel-filtration and reverse-phase HPLC. The procedure used was essentially the same as the one briefly described above for the purification of ANP, except that the initial extraction and the gel-filtration stages were done in the presence of several protease inhibitors.

900 frozen rat atria (Rockland, Inc.) were ground in liquid nitrogen and homogenized using a polytron in 6 volumes (by weight) of 1M acetic acid, 1M HCl, 2.5 mM PMSF, 1 mM EDTA, 20 μg/ml each of leupeptin, pepstatin and aprotinin. After centrifugation the supernatant was filtered through wetted gauze and the pellet was rehomogenized in 4 volumes (by weight) (total of 10 volumes) of homogenizing buffer. After centrifugation the supernatant was filtered through gauze and pooled with supernatant from the first centrifugation. The supernatants (15 mL portions) were passed through wetted Sep Pak (Waters) cartridges. The effluent was collected (30 ml) and passed through a second Sep Pak cartridge. Each cartridge was washed with 10 ml 0.1% TFA and eluted with 3 ml 80% acetonitrile in 0.1% TFA. All eluted material was combined and lyophilized.

Lyophilized atrial extract was dissolved in 5 ml 1M acetic acid containing 1% NaCl and loaded onto a Biogel P10 column (2.5 cm × 40 cm) equilibrated with 1M acetic acid in 1% NaCl. The column was eluted isocratically at a flow rate of 0.8 ml/min. Absorbance, at 280 nm, of each fraction was determined and an RIA was performed using an aliquot of each fraction. Immunoreactive (IR) peak fractions 37-53 as shown in FIG. 1(a) were collected and dialyzed against 0.1% trifluoroacetic acid (TFA) (5L).

The IR fraction from Biogel P10 was applied to a Bydac $C_{18}$ semipreparative column (10 mm × 250 mm) equilibrated with 0.1% TFA. The column was eluted at a flow rate of 3 ml/min using a gradient of acetonitrile.

Figure 1B:
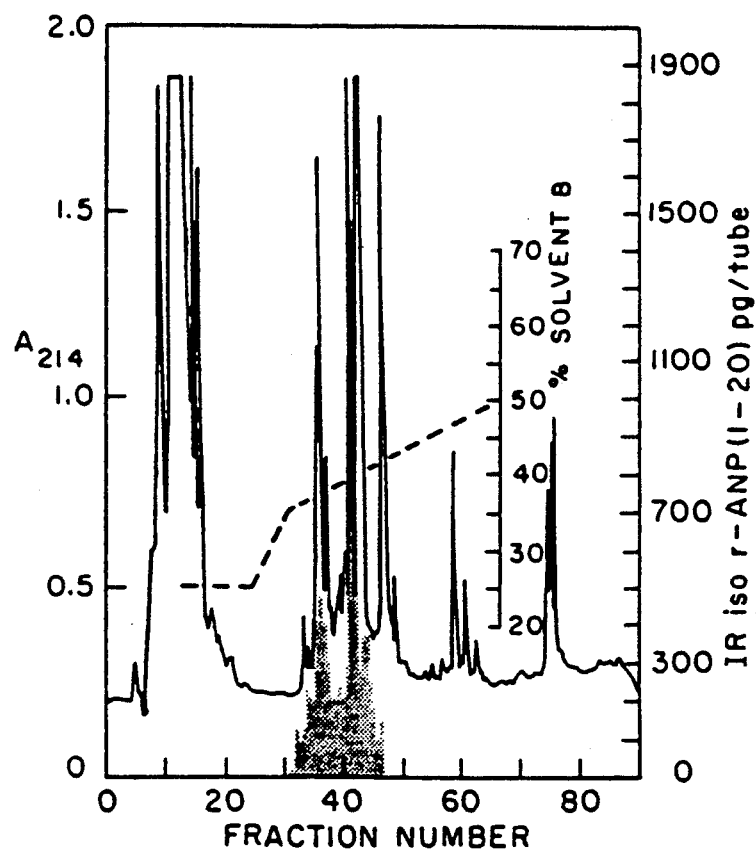
FIG. 1b is a chromatogram for the first reverse phase HPLC purification of the extract from FIG. 1(a)

The immunoreactive fraction coeluated with the peak at fractions 41-43 as shown in FIG. 1(b).

Figure 1C:
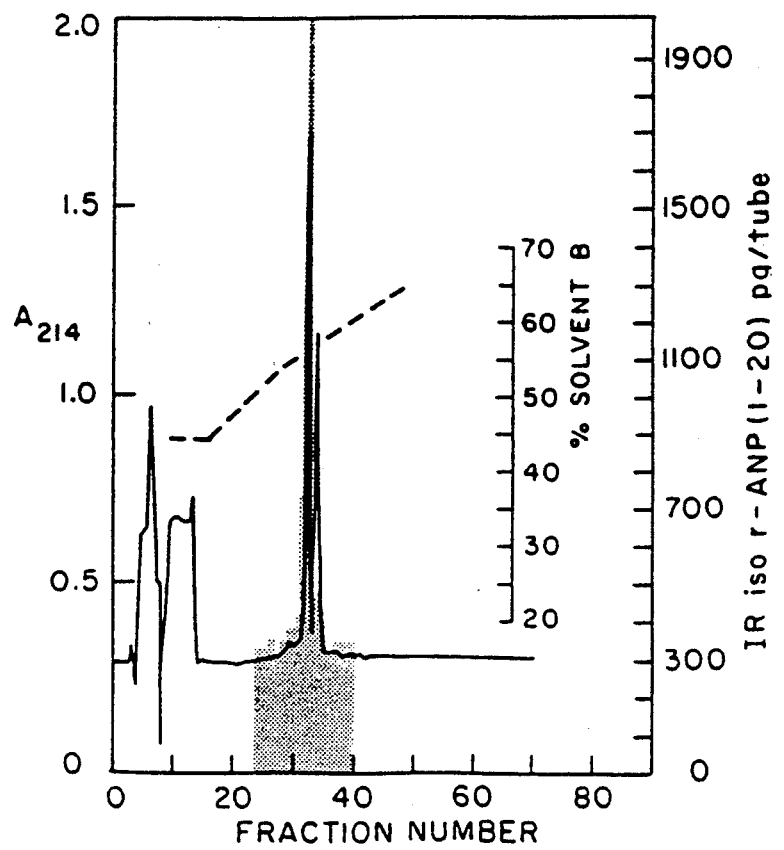
FIG. 1c is a chromatogram for the second reverse phase HPLC purification of the extract from FIG. 1(a)

The IR faction was further purified on a Vydac $C_{18}$ analytical column (4.6 mm × 250 mm) with a gradient of acetonitrile in the presence of 0.1% HFBA. IR peak as shown in FIG. 1(c) was collected in fractions 31-33.

Figure 1D:
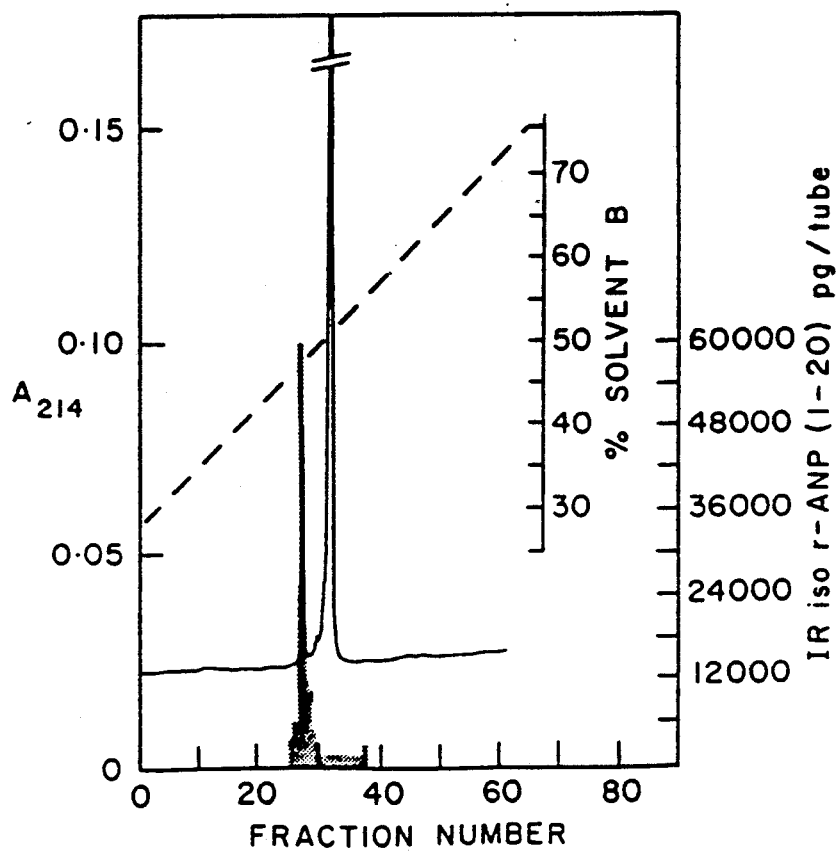
FIG. 1d is a chromatogram for the third reverse phase HPLC purification of the extract from FIG. 1(a)

The IR peak was then applied to a Vydac phenyl (4.6 mm × 250 mm) column and eluted with a gradient of acetonitrile in 0.1% TFA. IR iso-rANP as shown in FIG. 1(d) corresponds to the peak.

Figure 2:
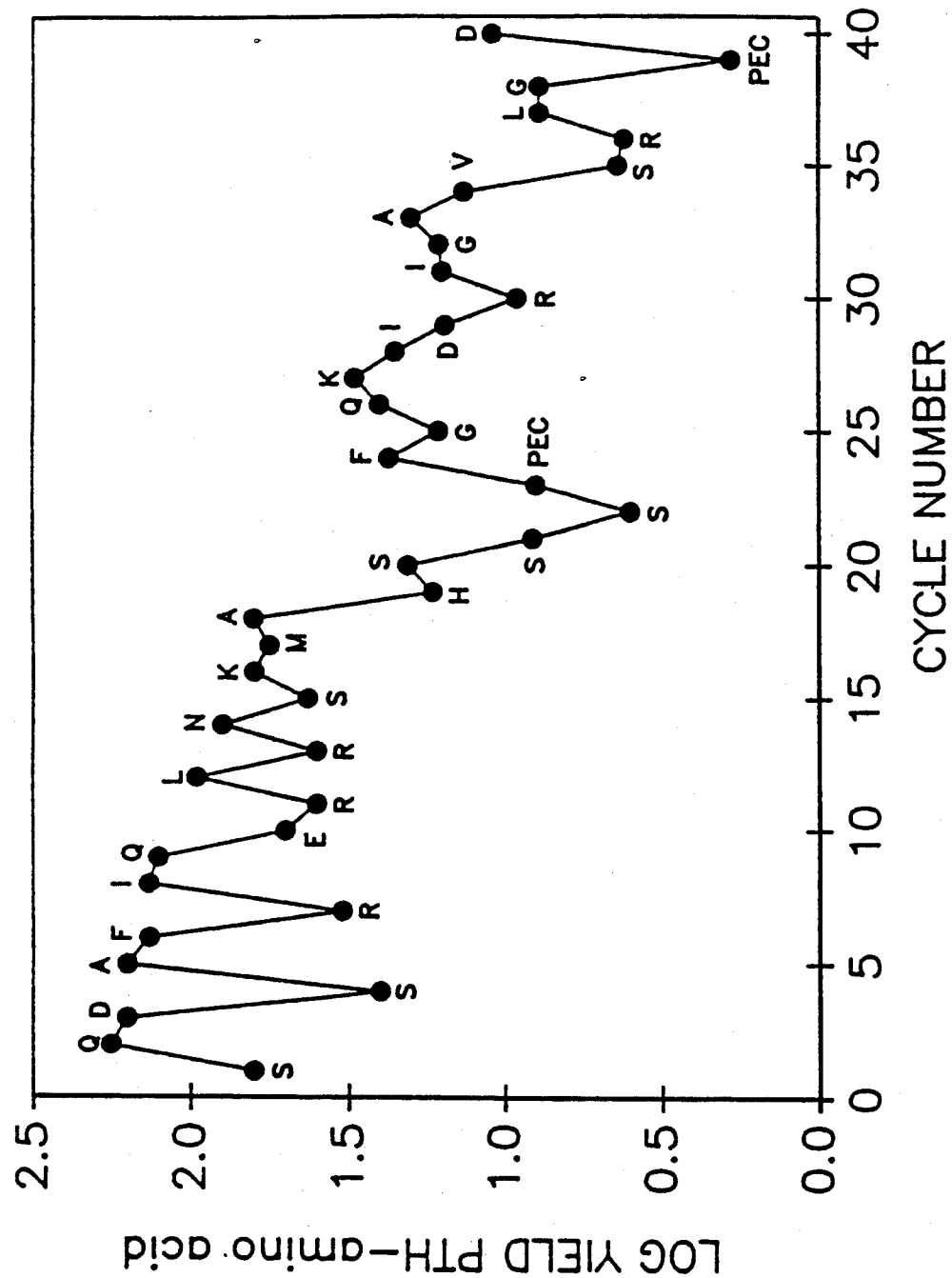
FIG. 2 is a graph illustrating repetitive yield of phenylthiohydantoin (PTH) amino acids liberated at each cycle of Edman degradation for the first 40 cycles of reduced pyridyelethylated iso-rANP(1-45)

The finally purified peptide appeared homogeneous by SDS gel electrophoresis, which indicated a molecular weight of about 5500. From the RIA it was estimated that the atria contain 0.7 ng/mg of iso-rANP which is considerably less than the value of about 175 ng/mg calculated for immunoreactive (IR) ANP in atria. The amino acid composition of the peptide was Cys-COOH (1.6); Asx (4.5); Ser (7.1); Glx (4.5); Gly (4.0); Ala (3.0); Met (0.84); Ile (3.72); Leu (2.97); Phe (2.85); His (0.9); Lys (2.2); Arg (5.7); indicating that the peptide was composed of 44-45 residues and contained two Cys residues. For sequencing, the peptide was reduced and pyridylethylated then subjected to sequencing, using a gas-phase automatic sequencer, and the complete amino acid sequence of the first 40 residues of the peptide was elucidated (FIG. 2). The sequence of the remaining residues and positive confirmation that the deduced structure contained a disulfide bond was obtained as follows. Purified, homogeneous native iso-rANP was subjected to proteolytic digestion with endoproteinase Lys C as previously described (19). The digested mixture was then subjected to chromatography by reverse phase HPLC using a $CH_3CN$/TFA gradient (12-50% solvent B over 30 min.). The elution profile showed two major peptide peaks, one (peak a) eluting at 18%, and the other (peak b) at 24% solvent B. The peptide in peak a contained a single sequence corresponding to residues 1-16 or iso-rANP. Sequencing of the material contained in peak b revealed a double sequence corresponding to residues 17-27 and residues 28-45. This extended the C-terminus of the peptide by 5 residues beyond that shown in FIG. 2 and is also what would be expected following cleavages at lys 16 and lys 27 if a disulfide bond was present. Subsequent cleavage of peak b with endoproteinase Lys C of reduced, pyridylethylated iso-$rANP_{(1-45)}$ followed by HPLC allowed the separation of two peptides with the expected sequences 17-27 and 28-45. Thus native iso-rANP consists of a 45 residue peptide with a disulfide bond between residues 23 and 29 (FIG. 3A).

Thus, it is clear that the 20 amino acid fragment, iso-$rANP_{(1-20)}$ constitutes the amino terminal end of a longer 45 residue peptide (FIGS. 2 and 3A). The 45 amino acids of this peptide maximally align with C-terminal portion of pro-ANP and pro-BNP, with striking homology exhibited within the disulfide bonded ring (FIG. 3B).

Little homology is shown between residues 1-20 of iso-$rANP_{(1-45)}$ and the amino terminal extension of $ANP_{(99-126)}$ i.e. residues 83-98 of pro-ANF. However, Lys 16 of iso-$rANP_{(1-45)}$ is homologous with Arg 98 of pro-ANP and represents a possible cleavage site. Residues 17-45 of iso-$rANP_{(1-45)}$ form a putative peptide which is both analogous and homologous to $ANP_{(99-126)}$ and to the recently discovered pig brain natriuretic peptide (BNP; FIG. 3B).

The iso-$rANP_{(17-45)}$, containing a disulfide linkage between the Cys residues, and iso-$rANP_{(1-45)}$ where residue 44=Gln were chemically synthesized using the method noted above.

Figure 4A:
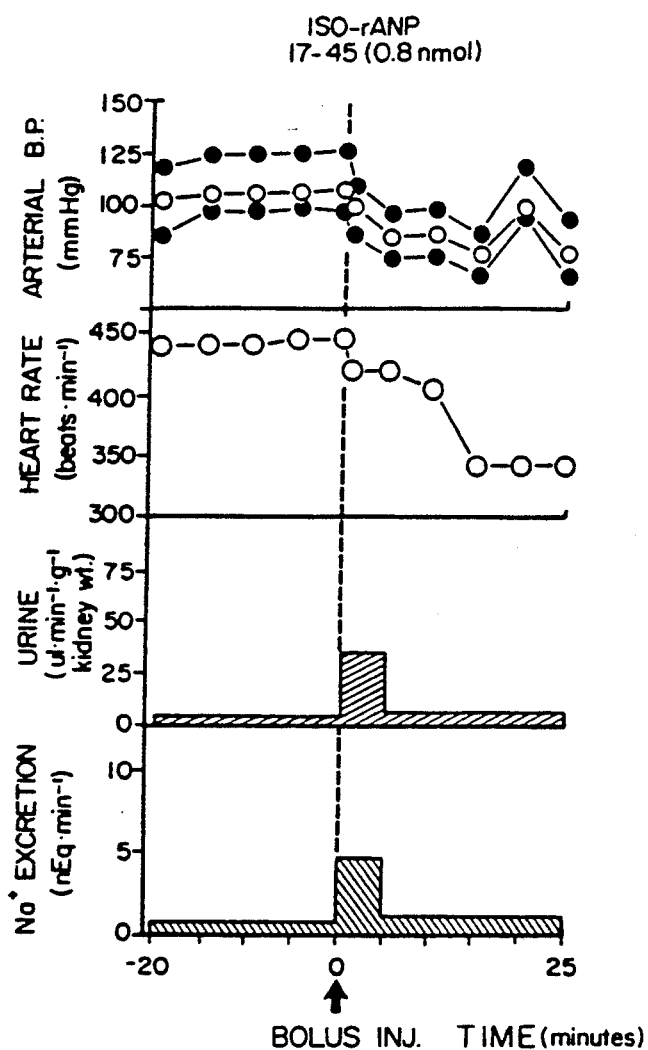
FIG. 4a and 4b are graphs showing effects of bolus injections (0.2 ml) of synthetic iso-rANP(17-45) and of iso-rANP(1-45) into pentobarbital anesthetized rats maintained on I.V. infusions of saline (1.2 ml h$^{-1}$), respectively
Figure 4B:
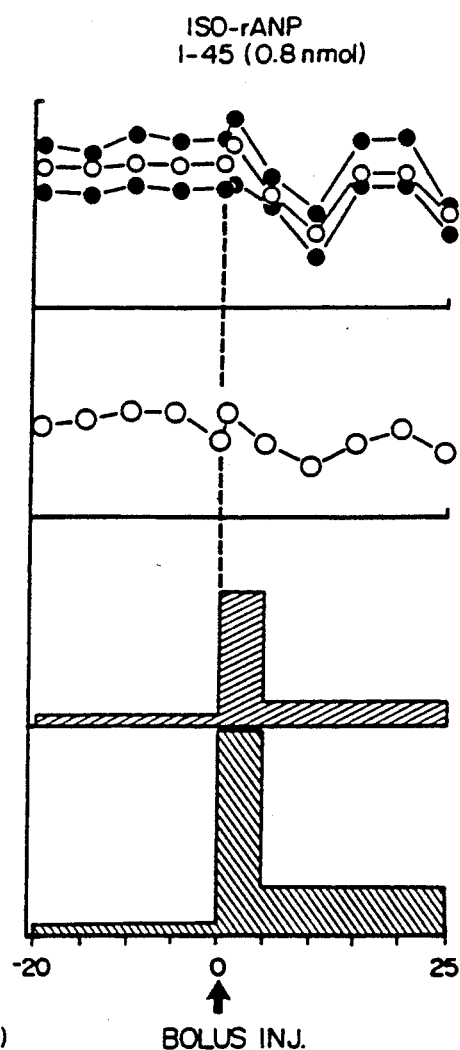

When injected into bioassay rats, both synthetic peptides elicited diuretic, natriuretic, hypotensive and bradycardic responses qualitatively similar to both the native peptide and rANP (FIG. 4 and Table 1).

surements were analyzed at 5 min intervals during control and at 1, 5, 10, 15 and 20 mins following administration of injectate. Injection of reduced pyridyllethylated iso-rANP$_{(1-45)}$ or iso-rANP$_{(17-45)}$ in the same concentration shown in FIG. 4 and Table 1 did not elicit a biological response. Thus, residues 17–45 of the native

TABLE 1

Peak cardiovascular and renal responses induced by I.V. bolus injections of native iso-rANP$_{(1-45)}$, and synthetic iso-rANP$_{(1-45)}$, iso-rANP$_{(17-45)}$ and rANP$_{(99-126)}$. Assay rats anesthetized with sodium pentobarbital and given a constant infusion of saline. All peak responses occurred within 10 min of injection. (average % change ± SEM)

| | Vehicle | native | synthetic | | |
|---|---|---|---|---|---|
| | (0.2 ml) | iso-rANP$_{(1-45)}$ | iso-rANP$_{(1-45)}$ | iso-rANP$_{(17-45)}$ | rANP$_{(99-126)}$ |
| Dose (nanomol) | 0 | 0.5* | 0.8 | 0.8 | 0.8 |
| % Decrease | | | | | |
| | (16) | (4) | (11) | (7) | (9) |
| MAP | −0.3 ± 2 | −17 ± 5† | −16 ± 3† | −12 ± 5† | −23 ± 4† |
| HR | −3 ± 2 | −9 ± 3† | −7 ± 2 | −28 ± 6† | −10 ± 2† |
| % Increase | | | | | |
| | (16) | (4) | | | (9) |
| Urine Volume | −1 ± 8 | +448 ± 230† | +828 ± 147†(11) | +412 ± 169†(7) | +586 ± 138† |
| Na$^+$ Excretion | −26 ± 10 | +592 ± 251† | +1009 ± 418 (5) | +597 ± 248 (6) | +1747 ± 580† |
| K$^+$ Excretion | −4 ± 7 | +545 ± 229† | +400 ± 129†(5) | +215 ± 109 (6) | +360 ± 115† |
| Cl$^-$ Excretion | +3 ± 10 | +344 ± 145† | +634 ± 139†(5) | +316 ± 148 (6) | +697 ± 183† |

Vehicle, 0.01M acetic acid, SEM, standard error of the mean; n in brackets is number of assay rats; MAP, mean arterial pressure; Hr, heart rate.
*Based on a molecular weight of approximately 5,000.
†p < 0.05 compared to vehicle.

Experiments were performed using male Sprague-Dawley rats, ranging in weight from 270–362 g. The rats were anesthetized by an intraperitional injection of sodium pentobarbital (70 mg.kg-1; MTC Pharmaceuticals, Hamilton, Ont.). Additional small amounts of anesthetic were administered as required in the course of the experiment. Body temperature was maintained by a heating lamp and rectal temperature monitored by a rectal probe. After installing a tracheal cannula, a femoral vein was cannulated and a priming infusion of saline (0.9% NaCl) was administered over a 20 min period (1.1 ml); this was followed by a maintenance saline infusion of 1.2 ml.h-1. The femoral artery was then cannulated for blood pressure measurement (Statham pressure transducer, model P23Db). A catheter was also advanced via the right external jugular vein towards the right heart for bolus injections of vehicle, ANF or the atrial peptide of the present invention (AHP). After tying off the penis, the bladder was cannulated for urine collection. Rates were not used or experiments aborted if the urine became bloody. The EKG was recorded for determination of heart rate.

Urine was collected in preweighed vials and volume calculated by weighing. The time for sequential urine collections was 5 min or, increments of 4 min until there was enough urine volume for electrolyte determinations (0.25 ml or 16 drops). Rat kidneys were removed at the termination of the experiments so that urinary excretion measurements could be normalized for total kidney weight. Measurements of Na+ and K+ were obtained using ion specific electrodes and Cl− was obtained by coulometric titration.

Zero time was established by 40-60 mins from the beginning the priming saline infusion. The control measurements were carried out over 20 mins or, until there was sufficient urine collection for electrolyte determinations. A bolus injection of vehicle, rANP$_{(99-126)}$ or iso-rANP$_{(1-45)}$ or iso-rANP$_{(17-45)}$ was then administered into the jugular vein catheter and the catheter immediately cleared of remaining injectate by a secondary bolus of 0.2 ml saline. The rANP$_{(99-126)}$ was obtained from Armand-Frappier, Montreal. Cardiovascular meapeptide represent a functional, as well as structural, homologue of both ANP and BNP. Moreover, it would appear that residues 1-20 of iso-rANP$_{(1-45)}$ are not required for biological activity. Also, synthetic iso-rANP$_{(1-20)}$ did not have any intrinsic biological activity. As shown in Table 1, the potency of iso-rANP$_{(17-45)}$ is somewhat less than rANP$_{(99-126)}$. It required twice the dose of iso-rANP$_{(17-45)}$ (1.5 nanomol) to produce equivalent average decreases in mean arterial blood pressure and heart rate as rANP$_{(99-126)}$ (0.7 nanomol). Furthermore, increasing the dose of iso-rANP$_{(17-45)}$ to 3.0 nanomol has no additional effect on these cardiovascular responses. With respect to urinary responses, at a dose level where rANP responses are maximal (0.7 nmol), 0.9 nmol of iso-rANP$_{(17-45)}$ had only a small effect in most rats. A four-fold larger dose of iso-rANP$_{(17-45)}$ (3.0 nanomol) than rANP$_{(99-126)}$ had a somewhat lesser effect in increasing urinary volume as well as Na+, K+ and Cl− excretion. Variability of response of assay rats to injected peptides is evident from the rather larger variances (SEM).

Both iso-rANP$_{(17-45)}$ and the native peptide, like rANP$_{(99-126)}$, showed smooth muscle vaso-relaxant acitivity.

Aortic rings (3–4 mm) were cut from the thoracic aortae of New Zealand White rabbits. The rings were suspended in a 10 ml tissue bath containing Kreb's Ringer Solution, pH 7.4 at 37° C. The rings were maintained at about 70% of maximal contraction with phenylephrine in doses ranging from $1 \times 10^{-6}$ to $5 \times 10^{-8}$M. Vasorelaxant activity or peptides was tested by adding various concentrations of peptide to the bath. Native iso-rANP$_{(1-45)}$ caused a slower and smaller relaxation of phenylephrine induced contraction of the rabbit throacic aortal rings compared to rANP$_{(99-126)}$.

The synthetic iso-rANP$_{(17-45)}$ was also less potent than ANP$_{(99-126)}$. A 20-fold higher dose was required to produce the same relaxation obtained by 50 ng of rANP$_{(99-126)}$. Reduced pyridyllethylated iso-rANP- (1-45) and iso-rANP(17-45) were devoid of smooth muscle vaso-relaxant activity.

Iso-rANP elicits weaker biological responses than rANP, but it is remarkable that it produces the biological responses it does, since the C-terminal portion of the peptide does not contain the Phe-Arg-Tyr sequence, which appear to be essential in rANP for maximal activity but it does contain an homologous arginine. This C-terminal sequence of rANP is also retained in BNP (FIG. 2C). The amino terminal extension of iso-rANP(17-45) bears little sequence homology to the amino terminal extension of ANP(99-126). The structure of the native peptide suggests that iso-rANP is, like rANP, derived from a larger precursor, which is genetically distinct from both ANP and BNP.

The existence of both iso-rANP and BNP indicates that there is a family of natriuretic peptides. BNP has only been found in brain, where it may act in concert with ANP in the control of water intake and salt appetite. Since a number of peptides originally discovered in brain have been shown to be present in other organs, it is possible that BNP occurs in other tissues also. Iso-rANP indicates that at least two natriuretic peptides are made by the heart. Iso-rANP may function in concert with rANP in regulating electrolyte and fluid balance and blood pressure and may compete for rANP kidney receptors. At least two kidney receptors for ANP have been demonstrated, one of which may be biologically silent.

Figure 5A:
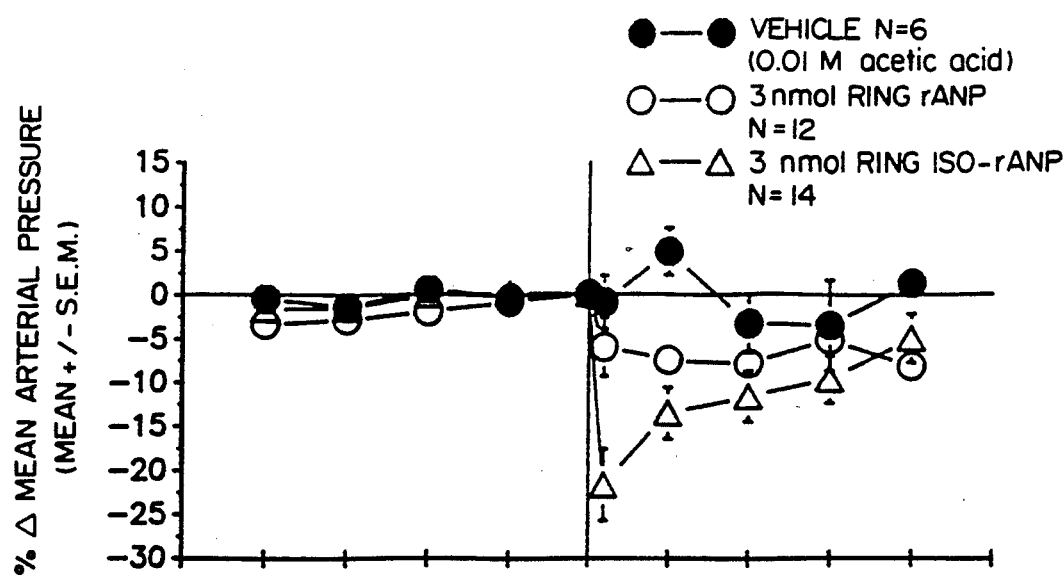
FIG. 5a, 5b, and 5c are graphs showing effects of bolus injections of 0.01M acetic acid, of 3 nmol ring rANP, and of 3 nmol ring iso-rANP, respectively
Figure 5B:
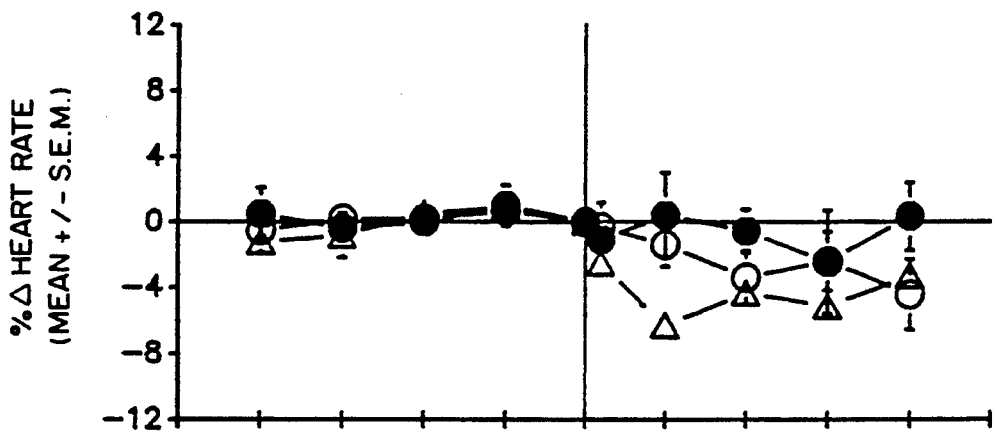
Figure 5C:
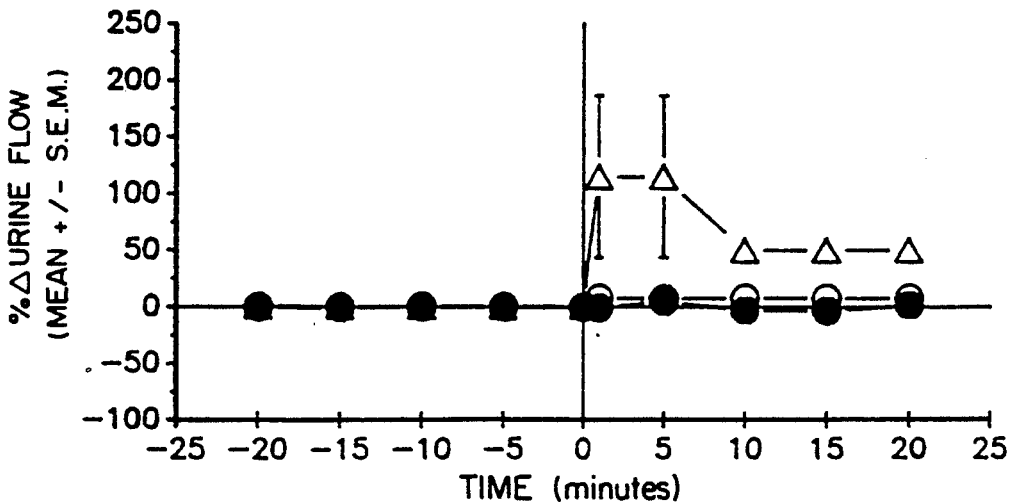

Iso-rANP$_{(23-39)}$, containing a disulfide linkage between the two Cys residues, was also chemically synthesized using the method described above. When injected into bioassay rats, this Iso-rANP$_{(23-39)}$ elicited a significant diuretic, natriuretic, hypotensive and bradycardin response (FIG. 5). These results are surprising when contrasted to the effect of injecting similar rats with similar quantities of rANP$_{(23-39)}$. While the ring portion of rANP appears to be substantially biologically inactive, the ring portion of Iso-rANP is active. The same protocols as described above were used in these tests and the results are statistically averaged in FIG. 5 for the vehicle (black circles) 0.01M acetic acid (6 rats), 3 nmol ring rANP (open circles) (12 rats) and 3 nmol ring iso-rANP (triangles) (14 rats).

We claim:

1. A peptide in substantially pure form selected from the group of peptides having the amino acid sequence: $R_1$-Ser-Ser-Cys-Phe-Gly-Gln-Lys-Ile-Asp-Arg-Ile-Gly-Ala-Val-Ser-Arg-Leu-Gly-Cys-Asp-$R_2$-$R_3$ and a disulphide double bond between said Cys and wherein $R_1$ is H, Ser, His-Ser, Ala-His-Ser, Met-Ala-His-Ser or Ser-Gln-Asp-Ser-Ala-Phe-Arg-Ile-Gln-Glu-Arg-Leu-Arg-Asn-Ser-Lys-Met-Ala-His-Ser, $R_2$ is Gly, Gly-Leu, Gly-Leu-Arg, Gly-Leu-Arg-Gln/Leu, or Gly-Leu-Arg-Gln/Leu-Phe and $R_3$ is OH.

2. A peptide as claimed in claim 1 wherein $R_1$ is Met-Ala-His-Ser and $R_2$ is Gly-Leu-Arg-Gln/Leu-Phe.

3. A peptide as claimed in claim 1 wherein $R_1$ is Ser-Gln-Asp-Ser-Ala-Phe-Arg-Ile-Gln-Glu-Arg-Leu-Arg-Asn-Ser-Lys-Met-Ala-His-Ser and $R_2$ is Gly-Leu-Arg-Gln/Leu-Phe.

4. A therapeutic composition of matter for producing natriuresis and diuresis, when injected into a non-diuretic rat, comprising a therapeutically effective amount of the peptide of claim 1 and a pharmaceutically acceptable carrier.

5. A therapeutic composition of matter for producing vascular smooth muscle relaxant activity comprising a therapeutically effective amount of the peptide of claim 1 and a pharmaceutically acceptable carrier.

6. A method of causing a diuretic, natriuretic, vasorelaxant or hypotensive response in a patient, comprising administering to said patient an effective amount of a peptide as claimed in claim 1.

7. A peptide in substantially pure form having an amino acid sequence comprising: H-Cys-Phe-Gly-Gln-Lys-Ile-Asp-Arg-Ile-Gly-Ala-Val-Ser-Arg-Leu-Gly-Cys-OH having a disulfide bond between said Cys residues.

* * * * *